United States Patent [19]
Stevenson et al.

[11] Patent Number: 5,853,381
[45] Date of Patent: Dec. 29, 1998

[54] ANKLE SUPPORT BRACE

[75] Inventors: Vernon Leslie Stevenson, Fort Worth; Kimberly Renee Douglas, Mansfield, both of Tex.

[73] Assignee: Tecnol Medical Products, Inc., Fort Worth, Tex.

[21] Appl. No.: 900,215

[22] Filed: Jul. 24, 1997

[51] Int. Cl.$^6$ ........................................... A61F 5/00
[52] U.S. Cl. ................................. 602/65; 602/27
[58] Field of Search .................. 602/27, 65, 66

[56] References Cited

U.S. PATENT DOCUMENTS

| | | |
|---|---|---|
| 640,755 | 1/1900 | Donavan . |
| 1,050,482 | 1/1913 | Mattler . |
| 1,798,271 | 3/1931 | Perugia . |
| 2,369,254 | 2/1945 | Roman . |
| 3,108,385 | 10/1963 | Teufel . |
| 3,333,304 | 8/1967 | Daddona, Jr. . |
| 4,323,058 | 4/1982 | Detty ........................... 602/27 |
| 4,527,556 | 7/1985 | Nelson ......................... 602/27 |
| 4,825,856 | 5/1989 | Nelson . |
| 4,960,135 | 10/1990 | Nelson . |
| 5,007,417 | 4/1991 | Bender ......................... 602/27 |
| 5,088,478 | 2/1992 | Grim . |
| 5,092,319 | 3/1992 | Grim . |
| 5,371,957 | 12/1994 | Gaudio . |
| 5,377,430 | 1/1995 | Hatfield et al. . |
| 5,657,767 | 8/1997 | Nelson et al. ............... 602/27 X |

FOREIGN PATENT DOCUMENTS 2596256  10/1987  France .

*Primary Examiner*—Linda C. M. Dvorak
*Attorney, Agent, or Firm*—Dority & Manning, P.A.

[57] ABSTRACT

An improved ankle support brace (10) is disclosed. The ankle support brace includes a first flexible lateral piece (12) and a second flexible lateral piece (14) attached to and disposed over the first lateral piece (12). The ankle support brace also inlcudes a first flexible medial piece 16) and a second flexible medial piece(18) attached to and disposed over the first medial piece (16). A first plurality of lace loops is disposed along a front edge of the first medial piece (16). Each of the first plurality of lace loops comprises a flexible material strip (56) attached at a plurality of points to the surface of the first medial piece (16). A second plurality of lace loops, each comprising a flexible material strip (50) attached at a plurality of points to a surface of the second medial piece (18), is disposed along a front edge of the second medial piece (18). A third plurality of lace loops (58), each comprising a flexible material strip (56) attached at a plurality of points to a surface of the first lateral piece (12), is disposed along a front edge (28) of the first lateral piece (12). A fourth plurality of lace loops (52), each comprising a flexible material strip (50) attached at a plurality of points to a surface of the second lateral piece (14), is disposed along a front edge (40) of the second lateral piece (14). A lace (24) is threaded through the first, second, third and fourth plurality of lace loops. The lace loops provide high-friction contact with the lace (24) and distribute tension from the tightened lace across the various surfaces of the ankle support brace.

15 Claims, 4 Drawing Sheets

ANKLE SUPPORT BRACE

TECHNICAL FIELD OF THE INVENTION

This invention relates generally to support braces and more particularly to ankle support braces that may be used for both athletic and medical purposes.

BACKGROUND OF THE INVENTION

For athletes engaging in certain high-impact sports, it is important that additional ankle support be provided to avoid injury. Preferably, the ankle support locks the heel against turning to prevent the ankle from being sprained or strained. Such support is also helpful for those recovering from ankle injuries.

Various ankle support braces have been developed to provide ankle support in both athletic and medical contexts. Two important qualities for such braces are the stability provided for the wearer's ankle and the durability of the brace itself, particularly when used in athletic activities.

Some known ankle support braces use a conventional footwear lacing arrangement in which a series of openings in the fabric on each side of the brace are used to hold the laces. The tension exerted when the laces are tightened is localized around these openings, creating the potential for rip-outs which cannot be easily repaired. This is of particular concern in ankle support braces, which must typically be tightened to fit very snugly and firmly around the wearer's ankle. The lace openings are therefore typically reinforced with metal eyelets, which may become disengaged from the brace material and lost, or may fail to prevent rip-outs under high stress.

SUMMARY OF THE INVENTION

Therefore, a need has arisen for an ankle support brace that addresses the disadvantages and deficiencies of the prior art.

An improved ankle support brace is disclosed. The ankle support brace comprises a first flexible medial piece and a second flexible medial piece attached to and disposed over the first medial piece. The ankle support brace also includes a first flexible lateral piece and a second flexible lateral piece attached to and disposed over the first lateral piece.

A first plurality of lace loops is disposed along a front edge of the first medial piece. Each of the first plurality of lace loops comprises a flexible material strip attached at a plurality of points to the surface of the first medial piece. A second plurality of lace loops is disposed along a front edge of the second medial piece. Each of the second plurality of lace loops comprises a flexible material strip attached at a plurality of points to a surface of the second medial piece. A third plurality of lace loops is disposed along a front edge of the first lateral piece. Each of the third plurality of lace loops comprises a flexible material strip attached at a plurality of points to a surface of the first lateral piece. A fourth plurality of lace loops is disposed along a front edge of the second lateral piece. Each of the fourth plurality of lace loops comprises a flexible material strip attached at a plurality of points to a surface of the second lateral piece. A lace is threaded through the first, second, third and fourth plurality of lace loops.

A technical advantage of the present invention is that the lace loops distribute tension from a tightened lace across the various surfaces of the ankle support brace, rather than at localized points. Another technical advantage is that the lace loops provide high-friction contact with the lace, thus preventing slippage of the lace during use.

BRIEF DESCRIPTION OF THE DRAWINGS

For a more complete understanding of the present invention and for further features and advantages thereof, reference is now made to the following description taken in conjunction with the accompanying drawings, in which.

DETAILED DESCRIPTION OF THE INVENTION

Figure 1:
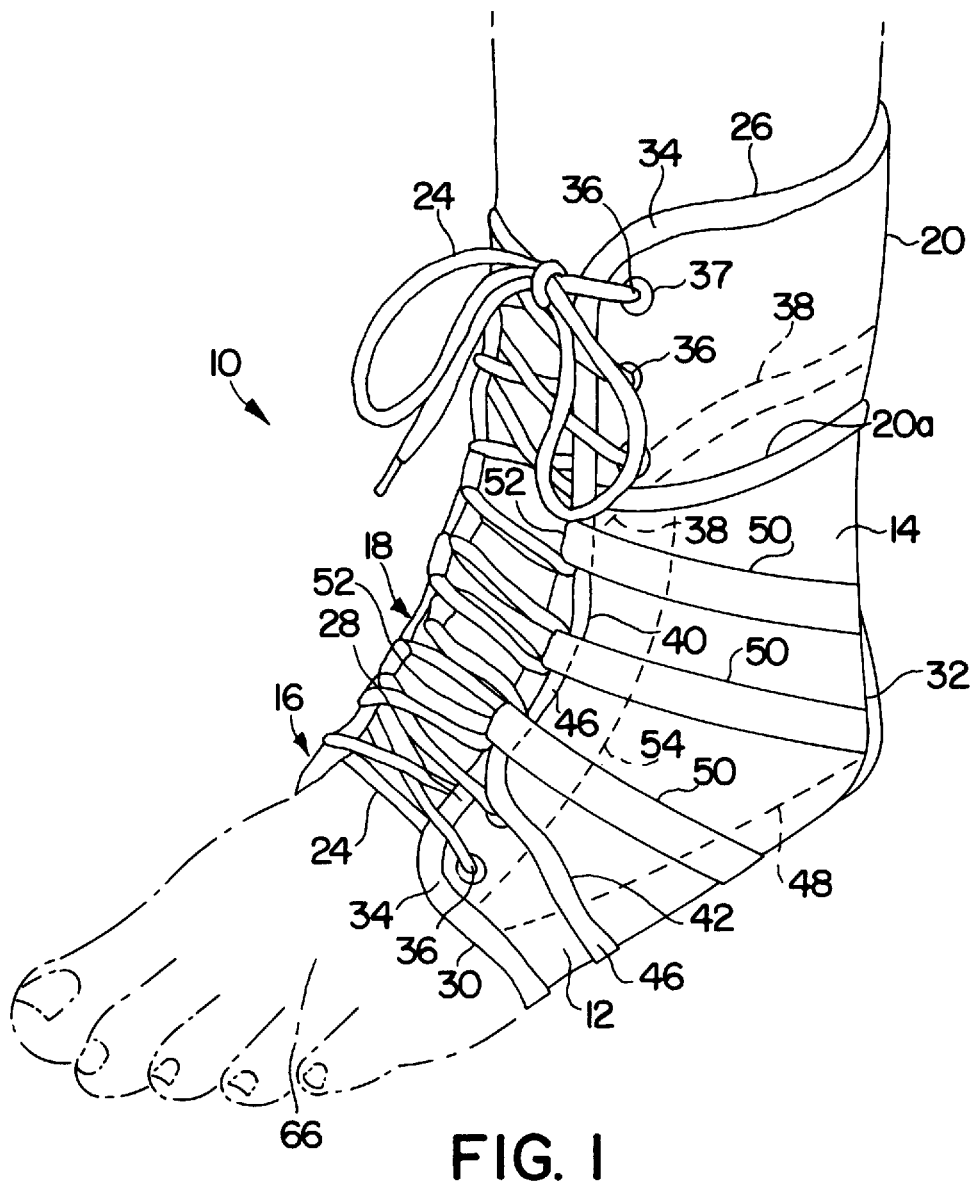
FIG. 1 is a perspective view of an ankle support brace in accordance with the present invention.
Figure 2:
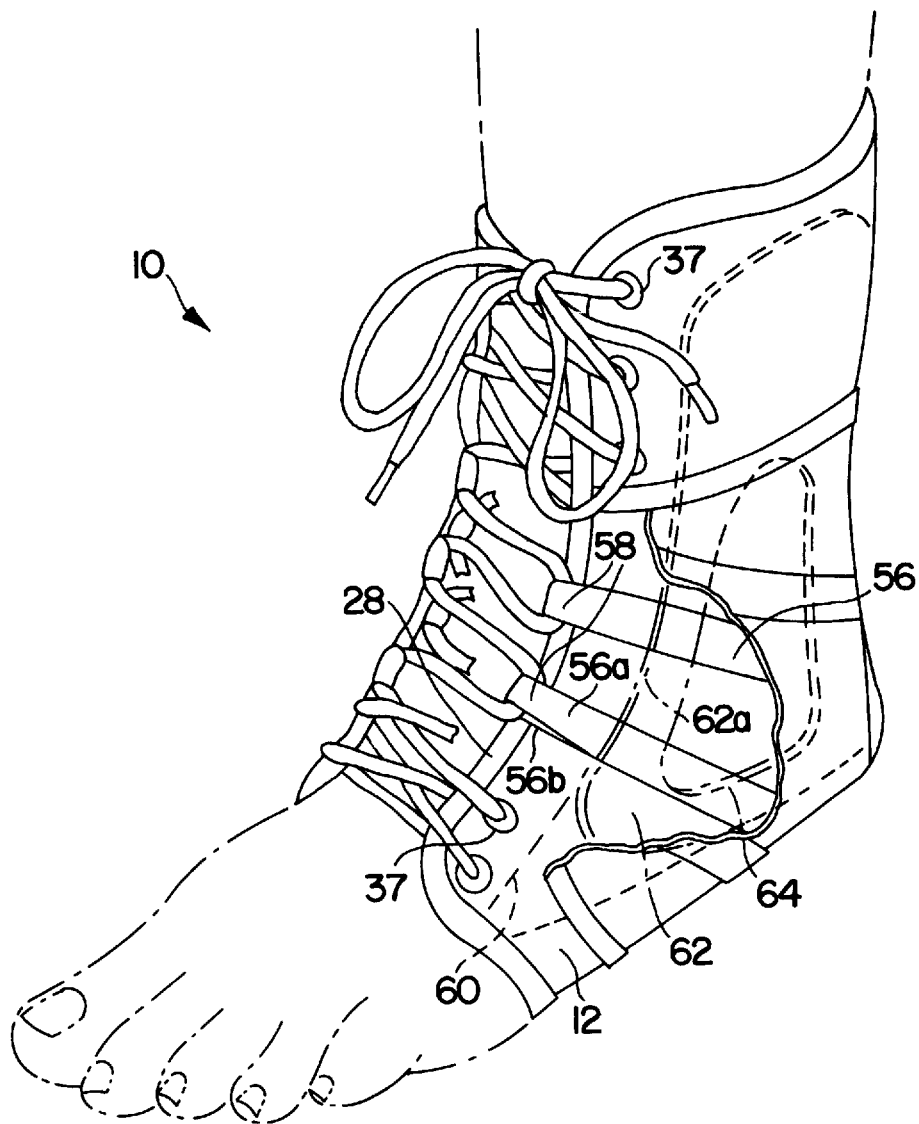
FIG. 2 is a perspective view of the ankle support brace with portions cut away.

Referring to FIGS. 1 through 4, an ankle support brace 10 constructed in accordance with the present invention is shown. Ankle support brace 10 comprises an inner lateral piece 12, an outer lateral piece 14, an inner medial piece 16, an outer medial piece 18, an upper piece 20, a rear connecting piece 22 and a lace 24.

Preferably, inner and outer lateral pieces 12 and 14 are identical to inner and outer medial pieces 16 and 18, so that ankle support brace 10 is bilaterally symmetric and may be worn on either foot. For purposes of illustration, therefore, only the lateral pieces 12 and 14 will be described in detail.

Inner lateral piece 12 preferably comprises a durable, flexible, substantially inelastic material such as vinyl, leather, canvas or the like. Inner lateral piece 12 may be lined on its inner surface with a padding material to cushion the wearer's ankle.

Inner lateral piece 12 has a top edge 26, a front edge 28, a forward edge 30, a bottom edge (not shown) and a back edge 32. A binding 34 is stitched along top edge 26, front edge 28 and forward edge 30. Inner lateral piece 12 has a plurality of openings 36 along the top and bottom portions of front edge 28 to hold lace 24. Openings 36 are reinforced by metal eyelets 37.

Outer lateral piece 14 preferably comprises a durable, flexible, substantially inelastic material such as vinyl, leather, canvas or the like. Outer lateral piece 14 has a top edge 38, a front edge 40, a forward edge 42, a bottom edge (not shown) and a back edge 44. A binding 46 is stitched along top edge 38, front edge 40 and forward edge 42.

Outer lateral piece 14 is attached to inner lateral piece 12 at various points. Back edge 44 of outer lateral piece 14 is stitched to back edge 32 of inner lateral piece 12 along the entire length of back edge 44. Likewise, the bottom edge of outer lateral piece 14 is stitched to the bottom edge of inner lateral piece 12 along its entire length. Outer lateral piece 14 is also stitched to inner lateral piece along a stitch line 48.

A plurality of canvas strips 50 are stitched to outer lateral piece 14 to form loops 52 capable of holding lace 24. Each strip 50 extends along the outer surface of outer lateral piece 14 to the back edge 44. Each strip 50 extends slightly beyond and loops over front edge 40 and extends along the inner surface of outer lateral piece 14 to stitch line 54. Each strip 50 is stitched to the outer surface of outer lateral piece 14 along both sides of the strip, from the back edge 44 of outer lateral piece 14 to binding 46 along the front edge 40 of outer lateral piece 14. Each strip 50 is also stitched to the outer surface of outer lateral piece 14 along stitch line 54 and at the edge of binding 46. Each strip 50 is stitched to the inner surface of outer lateral piece 14 along stitch line 54 and at the edge of binding 46.

Outer lateral piece 14 may be reinforced between stitch line 54 and front edge 40 by a semi-rigid plastic insert (not shown). This insert may be stitched into a pocket extending the entire length of front edge 40 and bounded by stitch line 54 on one side and by binding 46 along top edge 38, front edge 40 and forward edge 42. This insert serves to reinforce and stiffen outer lateral piece 14 at the primary points of attachment for loops 52.

A plurality of canvas strips 56 are stitched to inner lateral piece 12 to form loops 58 capable of holding lace 24. An overlying segment 56a of each strip 56 extends along the outer surface of inner lateral piece 12 to the back edge 32. An underlying segment 56b of each strip 56 extends underneath the overlying segment 56a along the outer surface of inner lateral piece 12, past stitch line 60. Each strip 56 is stitched to the outer surface of inner lateral piece 12 along the entire length of the strip from back edge 32 to stitch line 60. Each strip 56 is also stitched to the outer surface of inner lateral piece 12 along stitch line 60 and back edge 32. Strips 56 are placed so that loops 58 are positioned between loops 52 attached to outer lateral piece 12.

An open-top pocket is formed between inner lateral piece 12 and outer lateral piece 14. The bottom edge of this pocket occurs at stitch line 48, and the back edge is formed by the stitching securing back edges 32 and 44 together. Lace 24 forms a barrier along the front edge of the pocket.

Within this pocket is contained a semi-rigid plastic support insert 62. Support insert 62 is generally planar and triangular in shape, with a slightly concave front edge 62a. An opening 64 is formed in support insert 62. When ankle support brace 10 is placed on the wearer's foot 66, the wearer's ankle bone protrudes through opening 64. Support insert 62 serves to stiffen ankle support brace 10, thereby increasing the support provided by ankle support brace 10.

As previously described, medial pieces 16 and 18 are identical in construction to, and form a mirror image of, lateral pieces 12 and 14. The interconnection between these two symmetrical halves of ankle support brace 10 will now be described.

Figure 3:
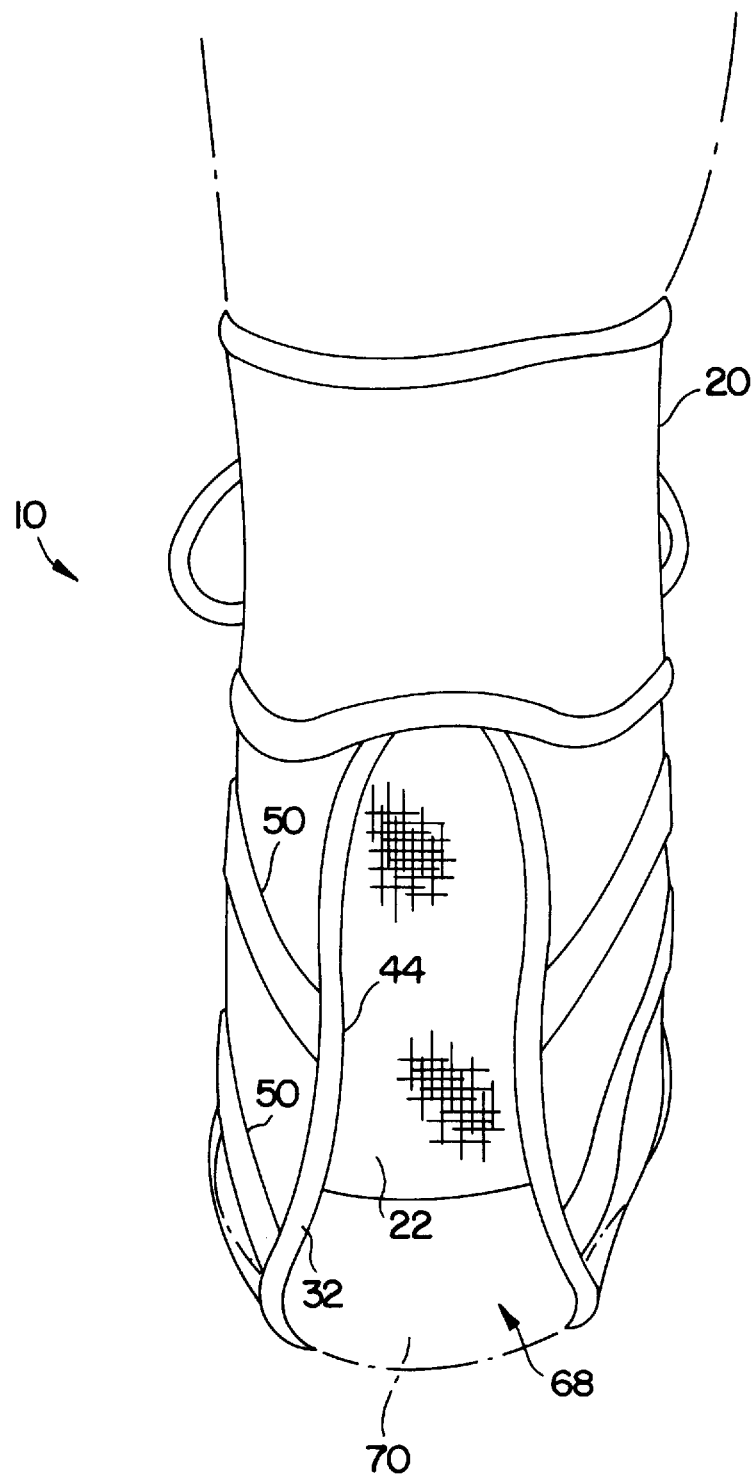
FIG. 3 is a rear view of the ankle support brace.
Figure 4:
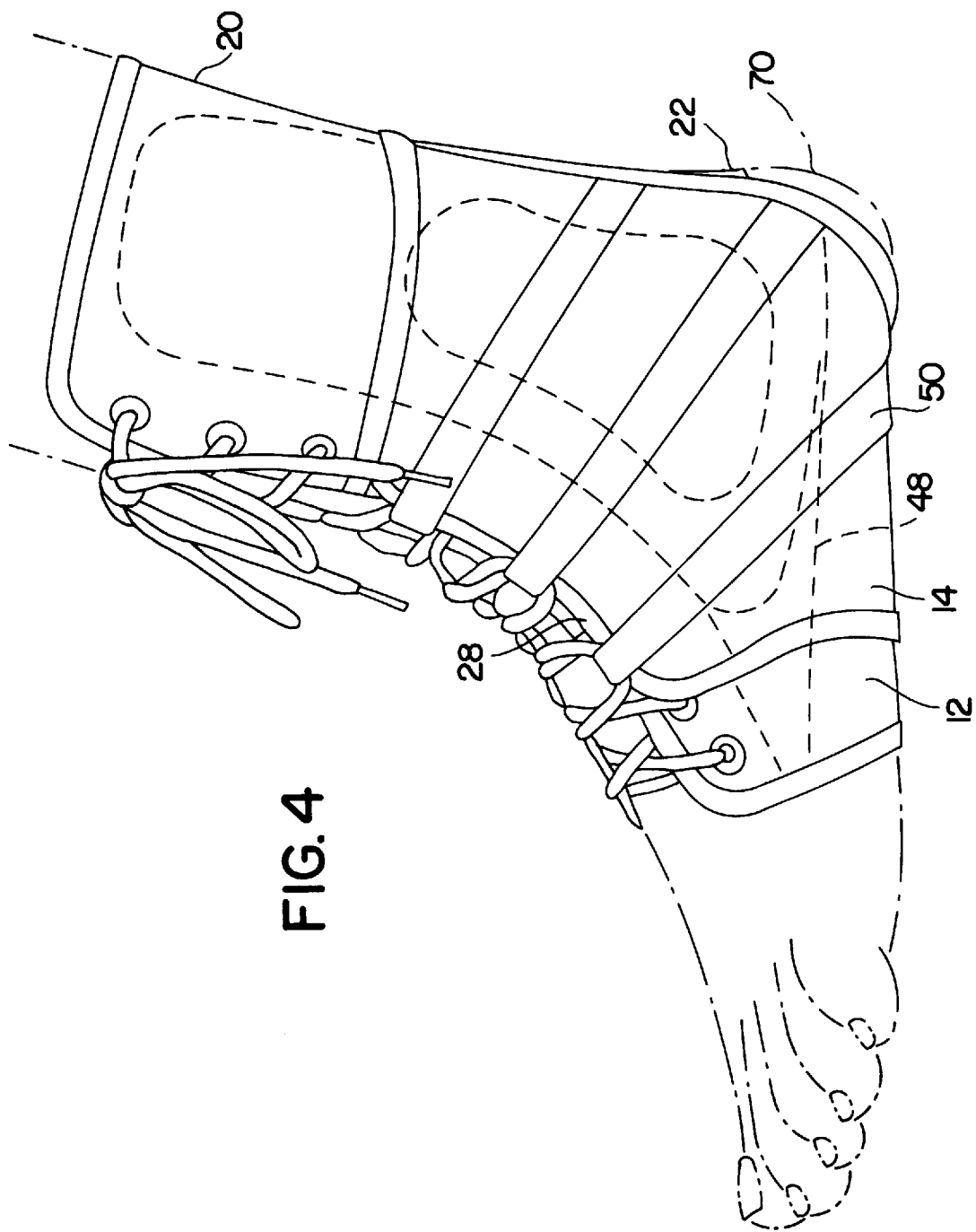
FIG. 4 is a side view of the ankle support brace.

Referring to FIG. 3, rear connecting piece 22 is stitched to lateral pieces 12 and 14 along a segment of back edges 32 and 44. Rear connecting piece 22 is likewise stitched to medial pieces 16 and 18 along a corresponding segment of the back edge. Rear connecting piece 22 preferably comprises an elastic material. Below rear connecting piece 22, the back edges of lateral and medial pieces 12 through 18 form an opening 68 through which the wearer's heel 70 protrudes.

Ankle support brace 10 may also have a front connecting piece (not shown) similar in construction to rear connecting piece 22. The front connecting piece, in addition to holding lateral and medial pieces 12 through 18 together, may cushion the wearer's foot 66 from lace 24.

Referring to FIG. 1, upper piece 20 is stitched to inner lateral piece 12 along top edge 26 and a segment of front edge 40. Upper piece 20 preferably comprises a durable, flexible, substantially inelastic material such as vinyl, leather, canvas or the like. Upper piece 20 has a plurality of openings corresponding to openings 36 of inner lateral piece 12. Each opening 36 of inner lateral piece 12, together with the corresponding opening of upper piece 20, is reinforced by a metal eyelet 37.

Upper piece 20 extends around the back of the wearer's leg and is similarly attached to inner medial piece 16 along its top and front edges. A bottom edge 20a of upper piece 20 overlaps the top edge 38 of outer lateral piece 14. Upper piece 20 therefore covers the open top of the pocket formed by inner and outer lateral pieces 12 and 14. The bottom edge 20a of upper piece 20 may be lifted up to provide access to this pocket for the removal or adjustment of support insert 62.

The bottom edges (not shown) of lateral and medial piece 12 through 18 come together beneath the wearer's foot 66. At this juncture, the edges are each stitched to a binding strip (not shown), which fastens the edges together.

The back edges of inner lateral and medial pieces 12 and 16 come together above rear connecting piece 22 and beneath upper piece 20. At this juncture, the edges may be fastened together with a binding strip as previously described with respect to the bottom edges of these pieces. Alternatively, inner lateral piece 12 and inner medial piece 16 may be cut as a unit from a single piece of material and thereby joined along this segment of their rear edges.

Lateral and medial pieces 12 through 18 are also connected by lace 24. As illustrated in FIG. 1, lace 24 is laced in a conventional manner through a lower set of openings 36 in inner lateral and medial pieces 12 and 16. One segment of lace 24 is then laced alternately through loops 52 of outer lateral piece 14 and the loops of inner medial piece 16. Another segment of lace 24 is laced alternately through the loops of outer medial piece 18 and loops 58 of inner lateral piece 12. Lace 24 is then laced in a conventional manner through the upper set of openings 36 in inner lateral and medial pieces 12 and 16 and upper piece 20.

When lace 24 is tightened, all four lateral and medial pieces 12 through 18 are pulled forward and together at the front of the wearer's foot and leg, with approximately the same tension being exerted on all four pieces 12 through 18. This tightening causes lateral and medial pieces 12 through 18 and the semi-rigid support inserts 62 on each side of the ankle to stabilize the ankle, thereby restricting the ankle from being sprained or strained when torque is applied during athletic or other activity.

The loop-and-lace arrangement described above provides various advantages over conventional ankle support braces. For example, the stitching that attaches strips 50 and 56 to lateral pieces 14 and 12, respectively, distributes the tension exerted by lace 24 on loops 52 and 58 across the surfaces of lateral pieces 14 and 12. This is in contrast to a conventional eyelet arrangement, in which all of the force exerted by the lace is localized at a series of points on the ankle brace, resulting in possible rip-outs of the lace openings. Ankle support brace 10 is therefore more durable than braces using conventional eyelet arrangements.

In addition, loops 52 and 58 engage lace 24 with more frictional contact than conventional metal eyelets. The additional friction between loops 52 and 58 and lace 24 reduces slippage of lace 24 after tightening, thus providing more stable support for the wearer's ankle.

It will be understood that various changes may be made to the relative positioning of loops 52 and 58 and the lacing technique described above without departing from the spirit and scope of the invention. In addition, while the invention has been particularly shown and described by the foregoing detailed description, it will be understood by those skilled in the art that various other changes in form and detail may be made without departing from the spirit and scope of the invention.

What is claimed is:

1. An ankle support brace comprising:

a flexible medial piece;

a flexible lateral piece connected to the medial piece;

a first plurality of lace loops disposed generally along a side of the medial piece operable to receive a lace, each of the first plurality of lace loops comprising a flexible material strip extending generally transversely across the medial piece to an opposite side and attached at a plurality of points to a surface of the medial piece; and a second plurality of lace loops disposed generally along a side of the lateral piece operable to receive the lace, each of the second plurality of lace loops comprising a flexible material strip extending generally transversely across the lateral piece to the opposite side and attached at a plurality of points to a surface of the lateral piece.

2. The ankle support brace of claim 1, further comprising a lace threaded through the first and second plurality of lace loops.

3. The ankle support brace of claim 1, wherein the medial piece and the lateral piece each comprise a plurality of openings operable to receive the lace.

4. The ankle support brace of claim 1, further comprising a connecting piece attached to and operable to connect the medial piece and the lateral piece.

5. The ankle support brace of claim 1, wherein the first plurality of lace loops is disposed along a front edge of the medial piece, and wherein the second plurality of lace loops is disposed along a front edge of the lateral piece.

6. The ankle support brace of claim 1, further comprising a rear connecting piece attached to and operable to connect a rear edge of the medial piece and a rear edge of the lateral piece.

7. The ankle support brace of claim 6, wherein the medial piece, lateral piece and rear connecting piece form an opening operable to receive a heel of a wearer's foot.

8. An ankle support brace comprising:

a first flexible medial piece having a front edge and a back edge;

a second flexible medial piece having a front edge and a back edge attached to and disposed over the first medial piece;

a first flexible lateral piece having a front edge and a back edge;

a second flexible lateral piece having a front edge and a back edge attached to and disposed over the first lateral piece;

a first plurality of lace loops disposed along the front edge of the first medial piece, each of the first plurality of lace loops comprising a flexible material strip extending generally transversely across the first medial piece to the back edge and attached at a plurality of points to a surface of the first medial piece;

a second plurality of lace loops disposed along the front edge of the second medial piece, each of the second plurality of lace loops comprising a flexible material strip extending generally transversely across the second medial piece to the back edge and attached at a plurality of points to a surface of the second medial piece;

a third plurality of lace loops disposed along the front edge of the first lateral piece, each of the third plurality of lace loops comprising a flexible material strip extending generally transversely across the first lateral piece to the back edge and attached at a plurality of points to a surface of the first lateral piece;

a fourth plurality of lace loops disposed along the front edge of the second lateral piece, each of the fourth plurality of lace loops comprising a flexible material strip extending generally transversely across the second lateral piece to the back edge and attached at a plurality of points to a surface of the second lateral piece;

a lace threaded through the first, second, third and fourth plurality of lace loops.

9. The ankle support brace of claim 8, further comprising a connecting piece attached to and operable to connect the medial pieces and the lateral pieces.

10. The ankle support brace of claim 9, wherein the medial pieces, the lateral pieces and the connecting piece form an opening operable to receive a heel of a wearer's foot.

11. The ankle support brace of claim 8, wherein the first and second lateral pieces form a pocket between an outer surface of the first lateral piece and an inner surface of the second lateral piece, the pocket being operable to receive a semi-rigid support insert.

12. The ankle support brace of claim 11, further comprising a semi-rigid support insert disposed in the pocket.

13. The ankle support brace of claim 11, further comprising a flexible upper piece attached to the first medial piece and the first lateral piece, the upper piece extending around the back edge of the first medial piece and the back edge of the first lateral piece, the upper piece forming an upper boundary of the pocket.

14. The ankle support brace of claim 8, wherein the first medial piece and the first lateral piece each comprise a plurality of openings operable to receive the lace.

15. The ankle support brace of claim 8, wherein the lace comprises:

a first segment threaded alternately through the first and fourth plurality of loops; and a second segment threaded alternately through the second and third plurality of loops.

* * * * *